United States Patent
Fujita et al.

(10) Patent No.: US 7,420,092 B2
(45) Date of Patent: Sep. 2, 2008

(54) PROCESS FOR PRODUCING ALDEHYDE

(75) Inventors: Yuichi Fujita, Yokkaichi (JP); Fumitaka Utsumi, Kurashiki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 121 days.

(21) Appl. No.: 11/267,505

(22) Filed: Nov. 7, 2005

(65) Prior Publication Data

US 2006/0189832 A1 Aug. 24, 2006

Related U.S. Application Data

(63) Continuation of application No. PCT/JP2004/006070, filed on Apr. 27, 2004.

(30) Foreign Application Priority Data

May 7, 2003 (JP) .............................. 2003-129306

(51) Int. Cl.
*C07C 45/50* (2006.01)

(52) U.S. Cl. ...................................... 568/451; 568/454

(58) Field of Classification Search ....................... None
See application file for complete search history.

(56) References Cited

U.S. PATENT DOCUMENTS

| 3,487,112 | A * | 12/1969 | Paulik et al. | ................. 568/454 |
| 6,492,564 | B1 * | 12/2002 | Wiese et al. | ................. 568/451 |
| 2001/0003785 | A1 | 6/2001 | Protzmann et al. | .......... 568/451 |

FOREIGN PATENT DOCUMENTS

| JP | 2-174740 | 7/1990 |
| JP | 2001-163820 | 6/2001 |

* cited by examiner

*Primary Examiner*—Sikarl A Witherspoon
(74) *Attorney, Agent, or Firm*—Oblon, Spivak, McClelland, Maier & Neustadt, P.C.

(57) ABSTRACT

A process by which a hydroformylation reaction can be efficiently conducted without lowering the yield of an aldehyde in the reaction is provided. A process for producing an aldehyde which includes subjecting an olefin to a hydroformylation reaction with carbon monoxide and hydrogen in the presence of a catalyst, characterized in that the olefin is fed as a gas to a reactor. In feeding the olefin as a gas to the reactor, it is preferred to gasify the olefin with the heat of the hydroformylation reaction.

20 Claims, 1 Drawing Sheet

PROCESS FOR PRODUCING ALDEHYDE

TECHNICAL FIELD

The present invention relates to a process for producing an aldehyde. More particularly, the invention relates to a process for producing an aldehyde by subjecting an olefin to a hydroformylation reaction with carbon monoxide and hydrogen in the presence of a catalyst.

BACKGROUND ART

Processes for producing aldehydes by the hydroformylation of olefins in the presence of a catalyst have been known and have been commercialized all over the world.

There are many known documents concerning those hydroformylation reactions, and the pressures in industrial hydroformylation reactions have usually been about from 2 MPaG to 20 MPaG and are about 1 MPaG even in the case of reduced-pressure processes. Consequently, C3 and C4 olefins under such industrial pressures have generally been fed as a liquid to the reactor because these olefins are liquid at ordinary temperature and a pressure of about 1 MPaG (see patent documents 1 to 3).

However, it was found that in a reactor to which a liquid olefin is continuously fed, the liquid level in the reactor is not stable under certain conditions and this may result in a behavior which is too unstable to control the progress of the hydroformylation reaction.

The causes for such troubles are thought to include the following: the feedstock olefin begins to increase in temperature in the reactor and gasifies abruptly; and the feedstock olefin comes to be present in excess locally and this causes a local reaction. The fluctuations in liquid level in the reactor are presumed to have occurred as a result of these.

Those unstable behaviors not only lower the yield in the target hydroformylation reaction but also make it impossible to control the liquid level in the reactor and the temperature. Efficient production cannot hence be realized.

[Patent Document 1] JP-A-61-218546
[Patent Document 2] JP-A-3-204831
[Patent Document 3] JP-A-52-125103

DISCLOSURE OF THE INVENTION

An object of the invention is to provide a process by which a hydroformylation reaction can be efficiently conducted without lowering the yield of an aldehyde in the reaction.

As a result of intensive investigations, the present inventors have found that the problems described above can be eliminated by gasifying a feedstock olefin before a reactor and feeding the gasified olefin. The invention has been thus completed. Essential points of the invention reside in the following (1) to (5).

(1) A process for producing an aldehyde which comprises subjecting an olefin to a hydroformylation reaction with carbon monoxide and hydrogen in the presence of a catalyst, characterized in that the olefin is fed as a gas to a reactor.

(2) The process as described under (1) above wherein the olefin is gasified with the heat of the reaction before being fed to the reactor.

(3) The process as described under (1) or (2) above wherein the olefin has 2-8 carbon atoms.

(4) The process as described under (1) or (2) above wherein the olefin is ethylene, propylene, or 1-butene.

(5) The process as described under any one of (1) to (4) above wherein the catalyst is a rhodium complex catalyst including a trivalent organophosphorus compound as a ligand.

BEST MODE FOR CARRYING OUT THE INVENTION

Figure 1:
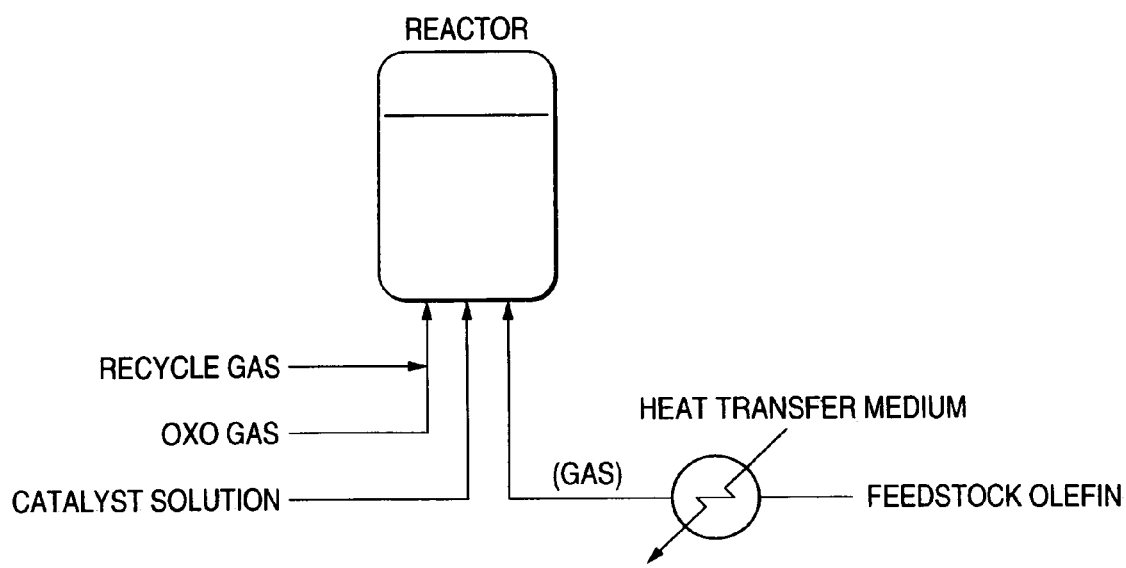
FIG. 1 is a view illustrating an example of methods of gasifying an olefin as a feedstock.

The invention will be explained below in detail.

The process of the invention is a process for producing an aldehyde which comprises subjecting an olefin to a hydroformylation reaction with carbon monoxide and hydrogen in the presence of a catalyst, and is characterized in that the olefin is fed as a gas to a reactor.

In the invention, a mixed gas comprising carbon monoxide and hydrogen is called an oxo gas.

<Feedstock>

The olefin to be used in the invention usually is a linear or branched α-olefin or an internal olefin, and preferably is an olefin having 2-8 carbon atoms. Examples thereof include ethylene, propylene, 1-butene, 1-hexene, 1-octene, 1-dodecene, and 1-tetradecene. More preferred is ethylene, propylene, or 1-butene. An especially preferred olefin is propylene.

<Catalyst>

The catalyst to be used in the invention is not particularly limited as long as it is a catalyst capable of converting olefins to aldehydes (hereinafter, this conversion is often referred to as hydroformylation). However, a rhodium catalyst including a trivalent organophosphorus compound as a ligand is preferred.

Examples of the trivalent organophosphorus compound include trivalent organophosphorus compounds having the ability to function as a unidentate ligand or multidentate ligand. Examples of the organophosphorus compounds functioning as a unidentate ligand include tertiary triorganophosphines represented by the following general formula (I).

(In general formula (I), R's each independently represents a substituted or unsubstituted, monovalent hydrocarbon group.)

Examples of the monovalent hydrocarbon groups generally include alkyl groups having 1-12 carbon atoms, cycloalkyl groups having 3-12 carbon atoms, aryl groups having 3-12 carbon atoms, alkylaryl groups having 6-24 carbon atoms, and arylalkyl groups having 6-24 carbon atoms. Namely, the triorganophosphines are, for example, trialkylphosphines, triarylphosphines, tricycloalkylphosphines, alkylarylphosphines, cycloalkylarylphosphines, alkylcycloalkylphosphines, and the like.

Substituents which may be possessed by the monovalent hydrocarbon groups are not particularly limited, and examples thereof include alkyl groups and alkoxy groups.

Specific examples of the triorganophosphines include tributylphosphine, trioctylphosphine, triphenylphosphine, tritolylphosphine, tricycloalkylphosphines, monobutyldiphenylphosphine, dipropylphenylphosphine, and cyclohexyldiphenylphosphine. A most preferred triorganophosphine is triphenylphosphine.

Other usable examples of the trivalent organophosphorus compound include trivalent phosphite compounds represented, for example, by the following formulae (1) to (10).

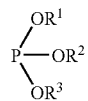 (1)

(In the formula, $R^1$ to $R^3$ each independently represents an optionally substituted monovalent hydrocarbon group.)

Examples of the optionally substituted monovalent hydrocarbon groups in formula (1) include alkyl groups, aryl groups, and cycloalkyl groups.

Specific examples of the compounds represented by formula (1) include trialkyl phosphites such as trimethyl phosphite, triethyl phosphite, n-butyl diethyl phosphite, tri-n-butyl phosphite, tri-n-propyl phosphite, tri-n-octyl phosphite, and tri-n-dodecyl phosphite; triaryl phosphites such as triphenyl phosphite and trinaphthyl phosphite; and alkyl aryl phosphites such as dimethyl phenyl phosphite, diethyl phenyl phosphite, and ethyl diphenyl phosphite. Also usable are bis(3,6,8-tri-t-butyl-2-naphthyl) phenyl phosphite and bis(3,6,8-tri-t-butyl-2-naphtyl) (4-biphenyl) phosphite, which are shown in, e.g., JP-A-6-122642, and the like. Most preferred of these is triphenyl phosphite.

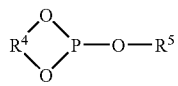 (2)

(In the formula, $R^4$ represents an optionally substituted divalent hydrocarbon group and $R^5$ represents an optionally substituted monovalent hydrocarbon group.)

Examples of the optionally substituted divalent hydrocarbon group represented by $R^4$ in formula (2) include alkylene groups which may contain one or more oxygen, nitrogen, or sulfur atoms or the like within the carbon chain; cycloalkylene groups which may contain one or more oxygen, nitrogen, or sulfur atoms or the like within the carbon chain; divalent aromatic groups such as phenylene and naphthylene; divalent aromatic groups formed by bonding divalent aromatic rings to each other directly or through an alkylene group or an atom such as oxygen, nitrogen, or sulfur; and groups formed by bonding a divalent aromatic group to an alkylene group directly or through an atom such as oxygen, nitrogen, or sulfur. Examples of the optionally substituted monovalent hydrocarbon group represented by $R^5$ include alkyl groups, aryl groups, and cycloalkyl groups.

Specific examples of the compounds represented by formula (2) include the compounds shown in U.S. Pat. No. 3,415,906, e.g., neopentyl (2,4,6-t-butylphenyl) phosphite and ethylene (2,4,6-t-butylphenyl) phosphite.

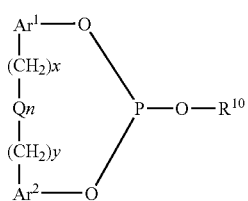 (3)

(In the formula, $R^{10}$ has the same meaning as $R^5$ in formula (2); $Ar^1$ and $Ar^2$ each independently represents an optionally substituted arylene group; x and y each independently represents 0 or 1; Q is a crosslinking group selected from the group consisting of $-CR^{11}R^{12}-$, $-O-$, $-S-$, $-NR^{13}-$, $-SiR^{14}R^{15}-$, and $-CO-$, wherein $R^{11}$ and $R^{12}$ each independently represents a hydrogen atom, an alkyl group having 1-12 carbon atoms, phenyl, tolyl, or anisyl and $R^{13}$, $R^{14}$, and $R^{15}$ each independently represents a hydrogen atom or methyl; and n represents 0 or 1.)

Specific examples of the compounds represented by formula (3) include the compounds shown in U.S. Pat. No. 4,599,206, e.g., 1,1'-biphenyl-2,2'-diyl (2,6-di-t-butyl-4-methylphenyl) phosphite, and the compounds shown in U.S. Pat. No. 4,717,775, e.g., 3,3'-di-t-butyl-5,5'-dimethoxy-1,1'-biphenyl-2,2'-diyl (2-t-butyl-4-methoxyphenyl)phosphite.

 (4)

(In the formula, $R^6$ represents a cyclic or acyclic, optionally substituted, trivalent hydrocarbon group.)

Specific examples of the compounds represented by formula (4) include the compounds shown in U.S. Pat. No. 4,567,306, e.g., 4-ethyl-2,6,7-trioxa-1-phosphabicyclo-[2,2,2]octane.

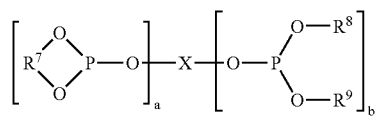 (5)

(In the formula, $R^7$ has the same meaning as $R^4$ in formula (2); $R^8$ and $R^9$ each independently represents an optionally substituted hydrocarbon group; a and b each represents an integer of 0 to 6, provided that the sum of a and b is 2 to 6; and X represents a hydrocarbon group having a valence of a+b.)

Preferred examples of the compounds represented by formula (5) include the compounds shown in JP-A-2-231497, e.g., 6,6'-[[3,3',5,5'-tetrakis(1,1'-dimethylethyl)-[1,1'-biphenyl]-2,2'-diyl]bis(oxy)]bisbenzo[d,f][1,3,2]dioxaphosphepin.

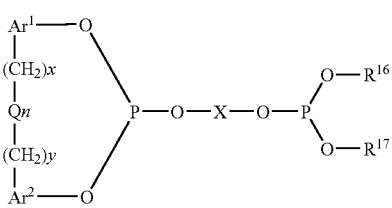 (6)

(In the formula, X represents a divalent group selected from the group consisting of alkylene, arylene, and $-Ar^1-(CH_2)_x-Q_n-(CH_2)_y-Ar^2-$; $R^{16}$ and $R^{17}$ each independently represents an optionally substituted hydrocarbon group; and $Ar^1$, $Ar^2$, Q, x, y, and n have the same meanings as in formula (3).)

Specific examples of the compounds represented by formula (6) include the compounds shown in JP-A-62-116535 and JP-A-62-116587.

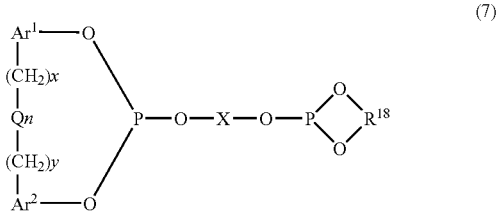

(In the formula, X, $Ar^1$, $Ar^2$, Q, x, y, and n have the same meanings as in formula (6); and $R^{18}$ has the same meaning as $R^4$ in formula (2).)

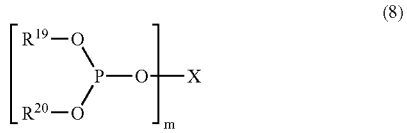

(In the formula, $R^{19}$ and $R^{20}$ each independently represents an aromatic hydrocarbon group, provided that at least one of the aromatic hydrocarbon groups has a hydrocarbon group bonded to a carbon atom adjacent to the carbon atom bonded to the oxygen atom; m represents an integer of 2 to 4; the $-O-P(OR^{19})(OR^{20})$ groups may be the same or different; and X represents an optionally substituted hydrogen group having a valence of m.)

Preferred examples of the compounds represented by formula (8) include the compounds shown in JP-A-5-178779 and the compounds shown in JP-A-10-45776, e.g., 2,2'-bis(di-1-naphthyl phosphite)-3,3',5,5'-tetra-t-butyl-6,6'-dimethyl-1,1'-biphenyl.

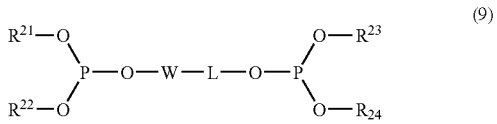

(In the formula, $R^{21}$ to $R^{24}$ represent an optionally substituted hydrocarbon group, provided that these may be independent of each other or $R^{21}$ or $R^{23}$ may be bonded respectively to $R^{22}$ or $R^{24}$ to form a ring; W represents an optionally substituted, divalent aromatic hydrocarbon group; and L represents an optionally substituted, saturated or unsaturated, divalent aliphatic hydrocarbon group.)

Usable examples of the compounds represented by formula (9) include those shown in JP-A-8-259578.

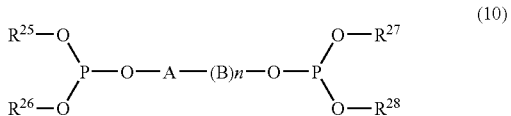

(In the formula, $R^{25}$ to $R^{28}$ represent an optionally substituted monovalent hydrocarbon group, provided that $R^{25}$ or $R^{27}$ may be bonded respectively to $R^{26}$ or $R^{28}$ to form a ring; A and B each independently represents a divalent aromatic hydrocarbon group which may have one or more substituents; and n represents an integer of 0 or 1.)

It is preferred that a source of rhodium, which serves as a component of the catalyst in the invention, be reacted in a solvent together with carbon monoxide, hydrogen, and a trivalent organophosphorus compound outside the reactor under the conditions of an elevated temperature and pressure to prepare a rhodium complex catalyst beforehand.

The solvent to be used in the catalyst preparation is selected generally from the reaction solvents which will be described later. However, this solvent need not be always the same as the reaction solvent. Conditions for the preparation are as follows. The rhodium concentration is generally 1 weight ppm or higher, preferably 10 weight ppm or higher, and is generally 10 wt % or lower, preferably 1 wt % or lower, more preferably 1,000 weight ppm or lower. Too low rhodium concentrations result in a lowered reaction rate and this may make it impossible to sufficiently conduct the reaction. On the other hand, too high concentrations result in an increased loss of rhodium, which is expensive. This is because when high-boiling components are purged, rhodium is discharged together with these. The proportion of the trivalent organophosphorus compound to the rhodium is generally 1-10,000, preferably 1-1,000, more preferably 1-100, in terms of phosphorus/rhodium molar ratio. When the proportion of the trivalent organophosphorus compound is too small, there are cases where the rhodium is not sufficiently stabilized because the amount of the compound coordinating to the rhodium is small. When the proportion thereof is too large, the concentration of the compound in the reaction system is too high and this results in an increased loss because when high-boiling components are purged, the compound is discharged together with these. The reaction temperature is generally 40° C. or higher, preferably 50° C. or higher, more preferably 60° C. or higher, and is generally 300° C. or lower, preferably 200° C. or lower, more preferably 150° C. or lower. Too low temperatures result in a lowered reaction rate and this may make it impossible to sufficiently conduct the reaction. On the other hand, too high temperatures may result in catalyst deactivation. The pressure for the reaction is generally 0.0001 MPaG or higher, preferably 0.01 MPaG or higher, more preferably 0.1 MPaG or higher, and is generally 20 MPaG or lower, preferably 10 MPaG or lower, more preferably 5 MPaG or lower. Too low pressures result in a lowered reaction rate and this may make it impossible to sufficiently conduct the reaction. Too high pressures necessitate an elevated design pressure for the preparation apparatus, resulting in an increased equipment cost. The treatment time is generally 5 minutes or longer, preferably 10 minutes or longer, more preferably 30 minutes or longer, and is generally 15 hours or shorter, preferably 5 hours or shorter, more preferably 3 hours or shorter. When the treatment time is too short, there are cases where the reaction does not proceed sufficiently and activity is not obtained. On the other hand, too long treatment times result in reduced catalyst activity.

The mode of reaction in the catalyst preparation may be batchwise or continuous.

<Method of Feeding Feedstock>

It is requisite in the invention to feed an olefin as a gas to the reactor.

Methods for feeding an olefin as a gas to the reactor are not particularly limited, and the feeding may be conducted with minimum necessary apparatus. A gaseous olefin may be fed to the reactor, or a liquid olefin may be gasified and fed to the reactor.

In the case where a liquid olefin is gasified and then fed to the reactor, it is economical to use, as the energy for gasifying the feedstock olefin, the heat of reaction in, e.g., the hydroformylation reaction (FIG. 2), the heat of a heat transfer medium transferred through a heat exchanger (FIG. 1), the heat energy possessed by the carbon monoxide and hydrogen to be used as feedstock gases, or the like. These may be used alone, or two or more of these may be simultaneously used in combination. From the standpoint of waste heat utilization (profitability), it is especially preferred to use the heat of reaction in the hydroformylation reaction.

Methods for gasifying a feedstock olefin will be explained in more detail by reference to the drawings.

Figure 2:
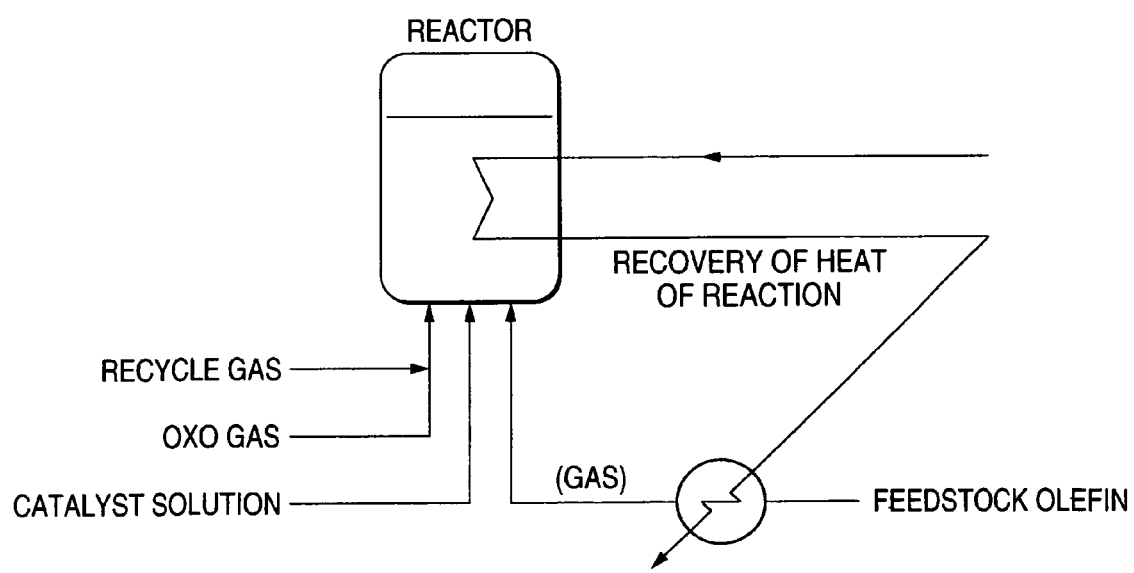
FIG. 2 is a view illustrating another example of methods of gasifying an olefin as a feedstock.

In FIG. 1 is shown a general method in which a feedstock olefin is gasified, before being introduced into a reactor, with the heat of a heat transfer medium transferred through a heat exchanger. In FIG. 2 is shown a method in which the heat of reaction is recovered from a reactor with a heat exchanger and this heat is used to gasify a feedstock olefin before the olefin is introduced into the reactor.

In the figures, the term oxo gas means a mixed gas comprising carbon monoxide and hydrogen as stated above, and the term recycle gas means a reaction product gas which has come out of the reactor and contains the oxo gas remaining unreacted.

<Solvent>

Solvents in which the catalyst dissolves and which exert no influence on the reaction can be used for the hydroformylation reaction. Examples thereof include condensates of the aldehyde yielded, aliphatic hydrocarbons such as hexane and octane, aromatic hydrocarbons such as toluene and xylene, alicyclic hydrocarbons such as cyclohexane, alcohols such as butanol, octanol, and polyethylene glycol, ethers such as triglyme, esters such as dioctyl phthalate, and water. Examples of the condensates of the aldehyde yielded include aldehyde trimers and tetramers. A paraffin having the same number of carbon atoms as the feedstock olefin may be used. Preferred solvents are toluene and condensates of the aldehyde yielded, from the standpoints of ease of separation from the reaction product and reduced influences on the reaction.

<Reaction Conditions>

Reaction conditions for the hydroformylation are as follows. The partial pressure of hydrogen is generally 0.0001 MPa or higher, preferably 0.01 MPa or higher, more preferably 0.1 MPa or higher, and is generally 20 MPa or lower, preferably 10 MPa or lower, more preferably 5 MPa or lower. Too low partial hydrogen pressures result in a lowered reaction rate, while too high partial hydrogen pressures result in increased generation of by-products.

The partial pressure of carbon monoxide is generally 0.0001 MPa or higher, preferably 0.01 MPa or higher, more preferably 0.1 MPa or higher, and is generally 20 MPa or lower, preferably 10 MPa or lower, more preferably 5 MPa or lower. In case where the partial carbon monoxide pressure is too low, the reaction does not proceed. In case where the partial carbon monoxide pressure is too high, the reaction does not proceed because of the partial pressure of the olefin is reduced.

The total pressure is generally 0.0001 MPaG or higher, preferably 0.01 MPaG or higher, more preferably 0.2 MPaG or higher, and is generally 50 MPaG or lower, preferably 30 MPaG or lower, more preferably 20 MPaG or lower. Too low total pressures result in a lowered reaction rate and this makes it impossible to sufficiently conduct the reaction. Too high total pressures necessitate an elevated design pressure for the reactor, resulting in an increased apparatus cost.

The partial hydrogen pressure/partial carbon monoxide pressure ratio is generally 0.1-100, preferably 0.1-10, more preferably 1-6. Too small values of this ratio result in insufficient progress of the reaction, while too high values thereof result also in insufficient progress of the reaction or in increased generation of by-products.

The reaction temperature is generally 20° C. or higher, preferably 40° C. or higher, more preferably 50° C. or higher, and is generally 200° C. or lower, preferably 150° C. or lower. Too low reaction temperatures result in insufficient progress of the reaction, while too high reaction temperatures may result in increased generation of by-products or in catalyst deactivation.

The rhodium concentration is generally 1 weight ppm or higher, preferably 10 weight ppm or higher, and is generally 10 wt % or lower, preferably 1 wt % or lower, more preferably 1,000 weight ppm or lower. Too low rhodium concentrations result in a lowered reaction rate and this makes it impossible to sufficiently conduct the reaction. Too high rhodium concentrations are uneconomical. This is because when high-boiling components are purged, rhodium is discharged together with these, resulting in an increased loss of rhodium, which is expensive.

The phosphorus (free organophosphorus ligand)/rhodium molar ratio is generally 0.1-10,000, preferably 0.1-1,000, more preferably 1-100. In case where the value of this ratio is too low, the rhodium is not sufficiently stabilized and there is the possibility that deactivation might occur. In case where that ratio is too high, the concentration of the organophosphorus compound in the reaction system is too high and this results in an increased loss because when high-boiling components are purged, the compound is discharged together with these.

The residence time is generally 1 minute or longer, preferably 10 minutes or longer, more preferably 20 minutes or longer, and is generally 24 hours or shorter, preferably 10 hours or shorter, more preferably 5 hours or shorter. In case where the reaction time is too short, the residence does not proceed sufficiently. In case where the residence time is too long, the formation of high-boiling components proceeds disadvantageously.

<Reactors>

The kinds of usable reactors are not particularly limited, and use can be made of the mixing vessel type, bubble tower type, plate column type, tubular type, gas stripping type, or the like. Usually, an olefin and an oxo gas as feedstocks and a catalyst solution are continuously fed to a continuous reactor to react the feedstocks under the hydroformylation reaction conditions described above. However, a batch reactor may be used. The reactor to be used may have an internal coil, jacket, external heat exchanger, or the like so as to maintain a constant reaction temperature. From the standpoint of liquid level stabilization, which is an effect of the invention, it is preferred to employ a mixing vessel type, bubble tower type, tubular type, gas stripping type, or similar reactor because improved reaction results brought about by liquid level stabilization are expected in such reactors. Especially when a mixing vessel type or gas stripping type reactor is used and fluctuations in liquid level occur, then the reactor should have a size having room for the fluctuations. Since liquid level stabilization makes it possible to conduct optimal sizing, such a reactor is suitable for the application of the invention thereto. On the other hand, when an overflow type bubble tower reactor or tubular reactor is used and the flow rate of the reaction product flowing out from the reactor fluctuates due to fluctuations in gas volume in the reactor, then it is necessary that the apparatus, e.g., a gas-liquid separator, to which the reaction product flowing out from the reactor is fed should be ones which have been designed so as to have a size having room for the fluctuations of the reaction product flow rate. Since stabilization of reaction product flow rate makes it possible to conduct optimal sizing of these apparatus, such a reactor is suitable for the application of the invention thereto. On the other hand, from the standpoint of the inhibition of local reactions, which is another effect of the invention, a reactor for isothermal reactions which has a heat-removing device, e.g., an internal coil, jacket, or external heat exchanger, is suitable for the application of the invention thereto.

As described above, by feeding an olefin as a gas to a reactor, the olefin can be inhibited from abruptly gasifying in the reactor upon heating to the reactor temperature, whereby the liquid level in the reactor can be prevented from fluctuating. Furthermore, local reactions are eliminated and a stable reaction temperature can be obtained. In addition, in the case of an overflow type reactor, the inhibition of fluctuations in liquid level in the reactor makes it possible to inhibit the amount of the reaction mixture fed to apparatus after the reactor, e.g., a gas-liquid separator, from fluctuating, and this leads to the stabilization of the liquid level in these apparatus.

EXAMPLES

The invention will be explained below in more detail by reference to Examples, but the invention should not be construed as being limited to the following Examples unless the invention departs from the spirit thereof.

In the following Examples and Comparative Examples, conversion and yield each was determined by the internal standard method through the analysis of a reaction mixture sample by gas chromatography.

Example 1

Into a 100-L reactor equipped with a stirrer were charged, with nitrogen replacement, 38.8 g of rhodium acetate, 15 kg of triphenylphosphine, and 70 L of toluene. While the contents were being stirred at a stirrer power of 1 kW/m$^3$, the pressure in the reactor was regulated to 1.7 MPaG with an oxo gas ($H_2/CO=1.02$) and the temperature of the liquid reaction mixture was adjusted to 70° C. with a heat transfer medium, etc. Thereafter, propylene feeding was initiated. First, propylene and the oxo gas were fed in amounts of 3.6 kg/H and an amount corresponding to the reaction, respectively. After the reaction temperature and the liquid level were ascertained to be stable, the feed rate of propylene was stepwise increased by 1 kg/H each time and that of the oxo gas was increased so as to correspond to the reaction. Until the propylene feed rate and the oxo gas feed rate reached the desired values of 7.2 kg/H and 7,700 NL/H, respectively, the feedstocks were stepwise fed to the reactor with heat removal so as to keep the temperature of the liquid reaction mixture at 100° C.

The propylene was gasified with an evaporator disposed just before the reactor and then fed through a piping separately disposed from the line for the oxo gas. After initiation of the feedstock feeding, the process gas (gas of reaction products containing the oxo gas remaining unreacted) which had come out of the reactor was always circulated and fed to the reactor. The rate of this feeding reached 3,000 L/H at the time when the propylene feed rate was the desired value.

Both the liquid level in the reactor and the reaction temperature were stable until the desired amounts were reached. After the reaction was conducted for 1 hour, the conversion of the propylene and the yield of an aldehyde were determined. As a result, the conversion and the aldehyde yield were found to be 95% and 93.5%, respectively.

Example 2

Propylene was reacted in the same manner as in Example 1, except that the propylene which had been gasified was caused to join the oxo gas before being fed to the reactor.

Both the liquid level in the reactor and the reaction temperature were stable.

Comparative Example 1

Propylene was reacted in the same manner as in Example 1, except that the propylene was not gasified. As a result, at the time when the propylene feed rate reached about 5 kg/H, the liquid level in the reactor rose abruptly and then dropped abruptly. All of the liquid level in the reactor, the pressure, and the temperature thus became unstable. Because of this, the feeding of the feedstock and oxo gas had to be stopped.

Comparative Example 2

Propylene was reacted in the same manner as in Example 2, except that the propylene was not gasified. As a result, the rates increased satisfactorily to high values. However, the liquid level in the reactor became unstable at around a propylene feed rate of 6 kg/H. Because of this, the feeding of the feedstock and oxo gas had to be stopped.

While the invention has been described in detail and with reference to specific embodiments thereof, it will be apparent to one skilled in the art that various changes and modifications can be made therein without departing from the spirit and scope thereof.

This application is based on a Japanese patent application filed on May 7, 2003 (Application No. 2003-129306), the contents thereof being herein incorporated by reference.

INDUSTRIAL APPLICABILITY

According to the invention, a process can be provided by which a hydroformylation reaction can be efficiently conducted without lowering the yield of an aldehyde in the reaction.

The invention claimed is:

1. A process for producing an aldehyde comprising:
   feeding an olefin as a gas to a reactor maintaining a stable liquid level in the reactor, and
   subjecting the gaseous olefin to a hydroformylation reaction with carbon monoxide and hydrogen in the presence of a catalyst in liquid reaction,
   wherein the reactor in which a stable liquid level is maintained is a mixing vessel or gas stripping reactor.

2. The process of claim 1, wherein the olefin is gasified with the heat of the reaction before being fed to the reactor.

3. The process of claim 1, wherein the olefin comprises 2-8 carbon atoms.

4. The process of claim 3, wherein the olefin is ethylene, propylene, or 1-butene.

5. The process of claim 1, wherein the catalyst is a rhodium complex catalyst comprising a trivalent organophosphorus compound as a ligand.

6. The process of claim 4, wherein the olefin is propylene.

7. The process of claim 1, wherein a solvent for dissolution of the catalyst is one selected from the group consisting of a condensate of the aldehyde yielded, an aliphatic hydrocarbon, an aromatic hydrocarbon, an alicyclic hydrocarbon, an alcohol, an ether, an ester and water.

8. The process of claim 7, wherein the solvent for dissolution of the catalyst is the condensate of the aldehyde yielded or toluene.

9. The process of claim 1, wherein a partial pressure of hydrogen is from 0.001 MPa to 20 MPa.

10. The process of claim 9, wherein the partial pressure of hydrogen is from 0.1 MPa to 5 MPa.

11. The process of claim 1, wherein a partial pressure of carbon monoxide is from 0.001 MPa to 20 MPa.

12. The process of claim 11, wherein the partial pressure of carbon monoxide is from 0.1 MPa to 5 MPa.

13. The process of claim 1, wherein a total pressure in the reactor is from 0.0001 MPaG to 50 MPaG.

14. The process of claim 13, wherein the total pressure in the reactor is from 0.02 MPaG to 20 MPaG.

15. The process of claim 1, wherein a ratio of partial hydrogen pressure to partial carbon monoxide pressure is from 0.1 to 100.

16. The process of claim 15, wherein the ratio of partial hydrogen pressure to partial carbon monoxide pressure is from 1 to 6.

17. The process of claim 1, wherein a reaction temperature is in the range 20° C. to 200° C.

18. The process of claim 17, wherein the reaction temperature is in the range 50° C. to 150° C.

19. The process of claim 5, wherein a rhodium concentration is from 1 ppm to 10 wt %.

20. The process of claim 19, wherein the rhodium concentration is from 1,000 ppm to 1 wt %.

* * * * *